United States Patent [19]

Fiege et al.

[11] 4,218,380
[45] Aug. 19, 1980

[54] PROCESS FOR THE PREPARATION OF ARYLGLYOXYLIC ACIDS

[75] Inventors: Helmut Fiege, Leverkusen; Karlfried Wedemeyer, Cologne; Kurt Bauer, Holzminden; Reiner Mölleken, Golmbach, all of Fed. Rep. of Germany

[73] Assignee: Bayer Aktiengesellschaft, Leverkusen, Fed. Rep. of Germany

[21] Appl. No.: 38,154

[22] Filed: May 11, 1979

[30] Foreign Application Priority Data

Jun. 3, 1978 [DE] Fed. Rep. of Germany ....... 2824407

[51] Int. Cl.$^2$ .................... C07D 317/06; C07C 51/33
[52] U.S. Cl. ............................... 260/340.5 R; 562/459
[58] Field of Search .................. 562/459; 260/340.5 R

[56] References Cited

PUBLICATIONS

Wiberg "Oxidation in Org. Chem." vol. 5-A (1965) p. 65.

*Primary Examiner*—Alan Siegel
*Attorney, Agent, or Firm*—Sprung, Felfe, Horn, Lynch & Kramer

[57] ABSTRACT

Novel process for the preparation of an arylglyoxylic acid compound, e.g., phenylglyoxylic acid, which comprises oxidizing an α-hydroxyarylacetic acid, e.g., mandelic acid, of the formula

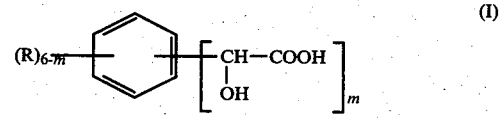

in which
  m is 1, 2 or 3,
  each R individually is hydrogen, alkyl, cycloalkyl, aryl, aralkyl, alkoxy, cycloakoxy, aryloxy, hydroxyl, halogen, aminoalkyl or carboxyl,
with the proviso that
  two R's together can represent the methylenedioxy group or a fused-on, optionally heterocyclic and optionally substituted ring,
with oxygen or a gas containing molecular oxygen in aqueous alkaline medium in the presence of a catalyst comprising a platinum-group metal in the presence as an activator of at least one of lead, a lead compound, bismuth and a bismuth compound at a temperature of up to the boiling point of the resulting reaction mixture.

31 Claims, No Drawings

PROCESS FOR THE PREPARATION OF ARYLGLYOXYLIC ACIDS

The present invention relates to a process for the preparation of certain arylglyoxylic acids. More specifically, the invention relates to the preparation of such arylglyoxylic acids by oxidation of α-hydroxyarylacetic acids (arylglycollic acids) with an oxygen-containing gas in alkaline medium in the presence of platinum-group metal catalyst.

Arylglyoxylic acids are valuable intermediates in organic snythesis, for example in the preparation of plant protection agents, of aromatic substances and flavoring agents and also of pharmaceuticals.

It is known that α-hydroxyarylacetic acids can be oxidized to arylglyoxylic acids; in particular mandelic acid can be oxidized to phenylglyoxylic acid. However, these oxidations require relatively expensive oxidizing agents which pollute the environment (such as potassium permanganate, chromium(VI) compounds, osmium(VIII) compounds and nitric acid), and operating conditions which have little attraction industrially. The oxidation is usually carried out with potassium permanganate in an aqueous alkaline medium. In this procedure, it is impossible to prevent, even under very favorable conditions (cooling with ice and concentrations of mandelic acid of less than 10% by weight), a considerable portion of the starting material being lost by over-oxidation (for example to benzoic acid) and the yields accordingly being unsatisfactory (see B. B. Corson et al, Organic Synthesis, Coll. Vol. I, 2nd edition (1956), page 241-245; according to this reference, yields of only 50-67% are achieved).

When mandelic acid is oxidized in aqueous solution with pure oxygen in the presence of sunlight, no phenylglyoxylic acid is obtained as a reaction product, but only benzaldehyde, salicylaldehyde, benzoic acid and a little salicylic acid (see G. Ciamician et al., Ber. dtsch, chem. Ges. 46, page 1,559 (1913)).

The present invention now provides a process for the preparation of an arylglyoxylic acid in which an α-hydroxy-arylacetic acid of the general formula

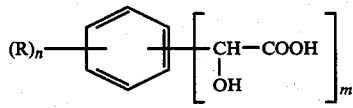

in which
m represents 1, 2 or 3,
n represents the number obtained from the difference (6-m) and
each R, independently of any other, represents hydrogen, alkyl, cycloalkyl, aryl, aralkyl, alkoxy, cycloalkoxy, aryloxy, hydroxyl, halogen, aminoalkyl or carboxyl, it being possible also for two R's together to represent the methylenedioxy group or a fused-on, optionally heterocyclic and optionally substituted ring,
is oxidized with oxygen or a gas that contains molecular oxygen an aqueous alkaline medium in the presence of a catalyst comprising a platinum-group metal (as hereinafter defined), in the presence as an activator, of lead and/or a compound thereof and/or bismuth and/or a compound thereof, and if appropriate in the presence of an inert organic solvent, at a temperature up to the boiling point of the reaction mixture.

The α-hydroxyaryl-acetic acids (I) can be in the D-form, the L-form or the D,L-form. Mixtures of various α-hydroxyaryl-acetic acids can also be employed for the oxidation.

If the starting compounds of the formula (I) contain more than one α-hydroxy-acetic acid groupings (m=2 or 3), the oxidation can also be conducted in a manner such that only one or two of the various α-hydroxyacetic acid groups are selectively oxidized to the glyoxylic acid group. Arylglyoxylic acids which possess one or two α-hydroxy-acetic acid groups are obtained in this manner.

The process according to the invention has a number of advantages. Thus, oxygen, which is generally available and cheap and does not lead to by-products which pollute the environment, is used as the oxidizing agent. It is of particular importance that the oxidation proceeds in a highly selective manner, scarcely leads to over-oxidations and thus gives considerably higher yields and purer products than the known processes; at the same time, this means that squandering of valuable raw materials is avoided. Finally, a further important advantage is that it is considerably easier to carry out the process industrially because the higher reaction temperatures make the removal of heat easier, the higher arylglyoyxlic acid concentrations make higher space/time yields and a more advantageous working up possible, the oxidation can easily be controlled via the uptake of oxygen and the separation and removal of problematical secondary products of oxidizing agents are eliminated.

With regard to the state of the art, it is to be described as decidedly surprising that it is possible to convert α-hydroxy-arylacetic acids, for example mandelic acid, into very pure arylglyoxylic acids, for example phenylglyoxylic acid, in very high yields in an industrially simple manner under the conditions of the process according to the invention. It is particularly surprising that, in contrast to the processes already known, the oxidation is highly selective and that no substantial over-oxidation, for example to benzoic acids, occurs.

When 3,4-methylenedioxy-mandelic acid is used as the starting compound, the course of the reaction can be represented by the equation which follows:

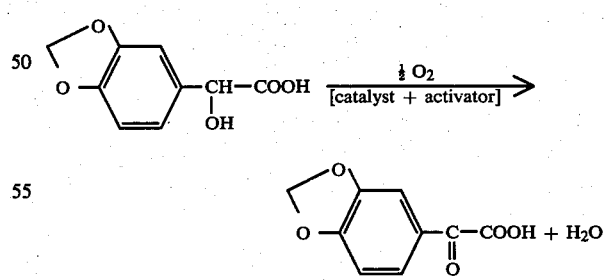

The formula (I) provides a general definition of the α-hydroxy-arylacetic acids to be used, according to the invention, as starting substances. Preferably, in this formula, m represents the number 1 and the R's independently of one another, each represent hydrogen, alkyl with 1 to 12 C atoms, cycloalkyl with 3 to 6 C atoms, phenyl, benzyl, alkoxy with 1 to 12 C atoms, cycloalkoxy with 3 to 6 C atoms, phenoxy, hydroxyl, fluorine, chlorine, bromine, iodine, aminoalkyl with 1 to 4 C atoms or the carboxyl group, it also being possible for two R's together to represent the methylenedioxy group.

Particularly preferred α-hydroxyarylacetic acids of the formula (I) are the compound in which m represents 1 and the R's all represent hydrogen (that is to say unsubstituted mandelic acid) and those compounds in which m represents 1 and either up to three R's, independently of one another, each represent alkyl with 1 to 6 C atoms (in particular methyl, ethyl, propyl, isopropyl, butyl, pentyl and hexyl), phenyl, benzyl, methoxy, ethoxy, isopropoxy, phenoxy, hydroxyl, carboxyl, fluorine, chlorine or bromine, or two R's together represent the methylenedioxy group, these radicals R being in the 3-, 4- and/or 5-position (that is to say certai mandelic acids which are mono-substituted, disubstituted and tri-substituted in the meta-position and/or para-position).

Specific examples of the compounds of the formula (I) are: mandelic acid, 3-methyl-mandelic acid, 4-methylmandelic acid, 3,4-dimethyl-mandelic acid, 3,5-dimethylmandelic acid, 3,4,5-trimethyl-mandelic acid, 3-ethylmandelic acid, 4-ethyl-mandelic acid, 3,4-diethylmandelic acid, 3,5-diethyl-mandelic acid, 3,4,5-triethylmandelic acid, 3-n-propyl-mandelic acid, 4-n-propyl-mandelic acid, 3,4-di-n-propyl-mandelic acid, 3,4,5-trin-propyl-mandelic acid, 3-i-propyl-mandelic acid, 4-i-propyl-mandelic acid, 3,4-di-isopropyl-mandelic acid, 3,5-di-isopropyl-mandelic acid, 3-n-butylmandelic acid, 4-n-butyl-mandelic acid, 3,4-di-n-butyl-mandelic acid, 3,5-di-n-butyl-mandelic acid, 3-sec.-butyl-mandelic acid, 4-sec.-butyl-mandelic acid, 4-tert.-butyl-mandelic acid, 3-hydroxy-mandelic acid, 4-hydroxy-mandelic acid, 3-hydroxy-4-methylmandelic acid, 4-hydroxy-3-methyl-mandelic acid, 4-hydroxy-3,5-dimethyl-mandelic acid, 4-hydroxy-5-isopropyl-mandelic acid, 4-hydroxy-3-methyl-5-isopropylmandelic acid, 4-hydroxy-5-tert.-butyl-mandelic acid, 4-hydroxy-3,5-di-tert.-butyl-mandelic acid, 3,5-dihydroxy-mandelic acid, 4-hydroxy-3-methoxy-mandelic acid, 4-hydroxy-3-ethoxy-mandelic acid, 3-hydroxy-4-methoxy-mandelic acid, 3,4-dimethoxy-mandelic acid, 3,4-methylenedioxy mandelic acid, 4-hydroxy-3,5-dimethoxy-mandelic acid, 3-phenoxy-mandelic acid, 4-phenoxy-mandelic acid, 3-methoxy-mandelic acid, 4-methoxy-mandelic acid, 3,5-dimethoxy-mandelic acid, 3-hydroxy-4-isopropoxy-mandelic acid, 4-hydroxy-3-isopropoxy-mandelic acid, 4-hydroxy-3-chloro-mandelic acid, 3-hydroxy-4-chloro-mandelic acid, 3-chloromandelic acid, 4-chloro-mandelic acid, 4-benzylmandelic acid, 3,4-dichloro-mandelic acid, 3,5-dichloro-mandelic acid, 3,4,5-trichloro-mandelic acid, 3-bromo-mandelic acid, 4-bromo-mandelic acid, 3,4-dibromo-mandelic acid, 3,5-dibromo-mandelic acid, 3-fluoro-mandelic acid and 4-fluoro-mandelic acid.

α-Hydroxyarylacetic acids of the formula (I) are in themselves known, or they can be prepared by known processes, for example by addition of hydrocyanic acid onto correspondingly substituted benzaldehydes and subsequent hydrolysis of the benzaldehyde cyanohydrins, or by saponification of 2,2-dihalogenoacetophenones (see. J. G. Aston et al., Org. Synth. Coll. Vol. III, 1955, page 538–541; further information on the synthesis is found in this reference, and in Rodd's Chemistry of Carbon Compounds volume III, Part E, 2nd edition (1974), page 105–109).

By "aqueous alkaline medium" it is to be understood that the α-hydroxyarylacetic acids are completely or partly present, during the oxidation, as alkali metal salts by reaction with an alkali in an aqueous medium. The amount of alkali can be chosen so that the reaction mixture has an alkaline reaction, that is to say a pH value >7. The alkali is advantageously used in amounts such that 0.3 to 5, preferably 0.5 to 2.5, equivalents of alkali are present per mole of carboxyl group in the α-hydroxyarylacetic acid. From 0.9 to 1.8 equivalents of alkali per mole of carboxyl group in the α-hydroxyarylacetic acid are most preferably used.

The alkali can be added to a solution or suspension of the α-hydroxyarylacetic acid in water, or the ≠-hydroxyarylacetic acid can be dissolved or suspended in the alkali solution.

The hydroxide or carbonate of sodium or potassium is preferably employed as the alkali.

In general, the concentration of the α-hydroxyarylacetic acids in the aqueous alkaline reaction solution is choosen so that both the α-hydroxyarylacetic acid and the arylglyoxylic acid formed are present in solution during the reaction. Concentrations of 5 to 40% by weight of α-hydroxyarylacetic acid have proved suitable. Nevertheless, it is also possible to oxidize suspensions. Mixtures of various α-hydroxyarylacetic acids can also be oxidized.

If α-hydroxyarylacetic acids which are sparingly soluble or insoluble in the aqueous alkaline reaction medium are used as starting compounds in the process according to the invention, and/or if the arylglyoxylic acids formed are sparingly soluble or insoluble in the aqueous alkaline solution, this may interfere with the oxidation. However, such interferences can as a rule be removed when the reaction is carried out in the presence of a solvent suitable for the sparingly soluble or insoluble compound.

Such a solvent can be completely miscible, partly miscible or even immiscible with the aqueous alkaline reaction medium. It is essential that the solvent is inert under the reaction conditions. Which solvent and what amount of solvent are to be used in an individual case can easily be determined by preliminary experiments. Possible solvents are both aprotic solvents, that is to say hydrocarbons, such as benzene and hexane, ethers, such as dioxan, or ketones, such as acetone, and protic solvents, especially alcohols, for example tert.-butanol.

Under the conditions according to the invention, an oxidation action can be observed at all temperatures at which a liquid aqueous phase is present. The possible reaction temperature accordingly extends from the solidifying point up to the boiling point of the reaction mixture. The reaction temperature to be applied in an individual case depends, inter alia, on the properties of the substances (such as the solubility and stability of the educts and products) and on industrial factors (desired rate of reaction and removal of heat). The oxidation is preferably carried out in the temperature range from 0° to about 100° C.

By "platinum-group metals" which are employed as catalysts in the process according to the invention there are to be understood the metals platinum, palladium, rhodium, iridium, ruthenium and osmium, which are closely related chemically and usually occur together in nature. The metals platinum and and palladium are preferably employed, in particular platinum.

The platinum-group metals used as the catalysts can be added to the reactants in the most diverse form for example in the elementar, that is to say metallic, form, for example as a so-called black, in combination with other platinum-group metals or in the form of compounds, for example as oxides or in the form of other compounds.

The platinum-group metals can also be applied to supports. Examples of suitable supports are active charcoal, graphite, kieselguhr, silica gel, spinel, aluminium oxide, asbestos, calcium carbonate, magnesium carbonate, barium sulphate or also organic support materials. Active charcoals, for example cheap pulverulent active charcoals, prepared from wood, which are frequently used for decoloration purposes, have proved particularly suitable.

The platinum-group metal content of these supported catalysts can vary within wide limits. Supported catalysts with a platinum-group metal content of less than 10% by weight, in particular those with platinum-group metal contents of 0.1 to 2.5% by weight, have proved particularly suitable.

The amounts in which the platinum-group metal catalysts are used can vary within wide limits. The amounts depend on the desired rate of oxidation, the nature of the α-hydroxyarylacetic acid to be oxidized, the form of the catalyst, the type and amount of activator and so on, and can easily be determined in a specific case by preliminary experiments. Thus, in the case of the oxidation of α-hydroxyphenylacetic acid in the presence of a lead compound as the activator, a phenylglyoxylic acid yield of 99% of theory is achieved in the course of 15 minutes when only 75 mg of platinum are present per mole of α-hydroxyphenylacetic acid. If longer oxidation times are accepted, it is also possible to carry out the oxidation in the presence of even smaller amounts of platinum, for example 30 mg of platinum per mole of α-hydroxyphenylacetic acid. In this case, the oxidation takes 70 minutes and the yield is likewise about 99% of theory.

In general, the amount of platinium-group metal required per mole of α-hydroxyacetic acid group is less than 500 mg, and in most cases sufficiently high rates of reaction are achieved with amounts of platinum of 10 to 150 mg per mole of α-hydroxyacetic acid group to be oxidized.

Since formation of tar is almost completely avoided when the activators according to the invention are used, the catalysts can be repeatedly employed. By re-using in this manner, it is possible to reduce the consumption of platinum-group metal catalyst to 3 mg and below per mole of α-hydroxyarylacetic acid before it becomes necessary to work up the platinum-group metal catalyst again.

Lead and/or bismuth, above all, have proved suitable activators. The amounts in which the activators to be used according to the invention are employed can vary within wide limits. The action of the activator already manifests itself significantly in the case of additions of $1 \times 10^{-6}$ mole of metal or metal compound per mole of α-hydroxyacetic acid group. It is also possible to employ 0.1 mole or more of activator per mole of α-hydroxyacetic acid group, but these high additions are in general of no advantage. Additions of $5 \times 10^{-6}$ to $1 \times 10^{-1}$ mole, preferably $1 \times 10^{-5}$ to $1 \times 10^{-2}$ mole, of metal per mole of α-hydroxyacetic acid group to be oxidized have in general proved suitable.

The metals to be used, according to the invention, as activators can be employed as such, that is to say in the elementary form, and/or in the form of their compounds, for example as oxides or salts of hydracids, such as chlorides, bromides, iodides, sulphides, selenides or tellurides, or as salts of inorganic oxyacids, such as nitrates, nitrites, phosphites, sulfates phosphates, carbonates, perchlorates, antimonates, arsenates, selenites, selenates or borates, or as salts or oxyacids which originate from transition metals, for example vanadates, niobates, tantalates, chromates, molybdates, tungstates or permanganates, or as salts of organic aliphatic or aromatic acids, for example formates, acetates, propionates, benzoates, salicylates, lactates, mandelates, glyoxylates, arylglyoxylates or citrates, or as phenolates and the like. The activators can in each case be soluble, partly soluble, or insoluble in the reaction mixture.

Combinations of these activators with one another and/or with other elements or compounds which are not specified as the activator can also be used. The activators according to the invention can be in various, and also mixed, valency stages; changes in valency can also occur during the reaction. If the activators are not already added in the form of oxides and/or hydroxides, it is possible to completely or partly convert them into these in an alkaline medium. After the reaction, the platinum-group metal catalyst can be filtered off with the sparingly soluble activator and re-used in further oxidations. Losses of platinum-group metal catalyst and/or activator are to be replaced as appropriate.

The activator can be added to the reactants as a solid, preferably in the finely divided form, or in the dissolved form. It is also possible to add the activator during the preparation of the platinum-group metal catalyst or to impregnate the platinum-group metal catalyst with the activator. The activator can also serve as a support material for the platinum-group metal.

The combination of platinum and lead and/or bismuth has proved particularly suitable.

The process according to the invention is usually carried out by bringing oxygen or a gas that contains molecular oxygen, such as air, into good contact with the solution of the α-hydroxyarylacetic acid containing the alkaline agent, the platinum-group metal catalyst and the activator according to the invention. The oxidation is usually carried out under atmospheric pressure (1 bar), but it is also possible to carry it out under higher or lower pressures, for example in the range from 0.5 to 10 bars. The course of the reaction can be followed via the amount of oxygen taken up and is interrupted when the amount of oxygen theoretically required for the desired arylglyoxylic acid has been taken up. In most cases, the uptake of oxygen ceases by itself in this stage, or it slows down. The progress of the reaction can also be followed in another manner, for example by determining the α-hydroxyarylacetic acid consumed or the arylglyoxylic acid formed.

For working up, the platinum-group metal catalyst and also undissolved activator are separated off from the reaction mixture, for example by filtration. The arylglyoxylic acids are liberated from the alkaline reaction solution by acidifying the solution to a pH value below 6, and are separated off by known processes, such as decanting, filtration, extraction and/or steam distillation, and if necessary are further purified, for example by recrystallization, distillation, extraction or sublimation.

The sequence in which the platinum-group metal catalyst, activator, alkali and α-hydroxyarylacetic acid are brought together is optional. Thus, the platinum-group metal catalyst and activator can be added to the aqueous alkaline hydroxyarylacetic acid solution; it is also possible to initially introduce the platinum-group metal catalyst and activator and to add the aqueous alkaline α-hydroxyarylacetic acid solution; finally, it is furthermore possible initially to introduce the platinum-group metal catalyst, some of the aqueous alkali and the activator and to add the α-hydroxyarylacetic acid together with the remainder of the alkali. Furthermore, it is possible to add the activator to the mixture of the reactants.

The arylglyoxylic acids which can be prepared by the process according to the invention are important organic intermediate products and are of great significance, for example, for the preparation of plant protection agents, of aroma substances and flavoring agents and of medicaments.

Thus, for example, herbicidally active compounds can be prepared starting from phenylglyoxylic acid (see DE-OS (German Published Specification) 2,224,161). For instance, 3-methyl-4-amino-6-phenyl-1,2,4-triazin-5(4H)one of the formula

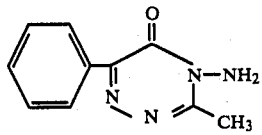

can be prepared by reacting phenylglyoxylic acid, in the presence of a mineral acid, such as sulphuric acid, with ethanol in a first stage and, in a second stage, reacting the resulting phenylglyoxylic acid ethyl ester with acetylhydrazine, whereupon 1-phenylglyoxyic acid ethyl ester-2-acetylhydrazone is formed, which, in a third stage, is converted, with hydrazine hydrate, in the presence of pyridine, into the above-mentioned end product. This multi-stage synthesis can be represented by the following equations:

1st stage:

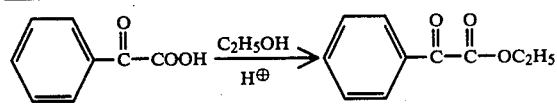

2nd stage:

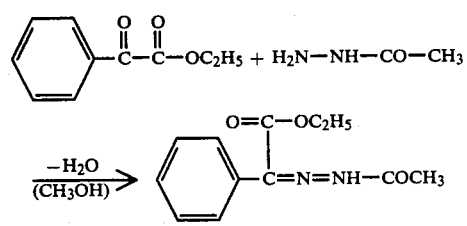

3rd stage:

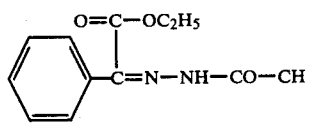

-continued

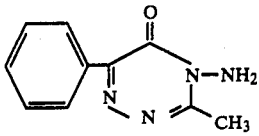

The process according to the invention is illustrated by the preparative Examples which follow.

EXAMPLE 1

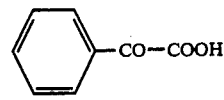

0.75 g of platinum-containing active charcoal (platinum content: 1% by weight), 0.5 ml of 0.1 molar Pb(NO$_3$)$_2$ solution (corresponding to an amount of lead of $5 \times 10^{-5}$ moles) and a solution of 15.2 g (0.1 mole) of D,L-mandelic acid in 100 ml of 1.2 N sodium hydroxide solution were introduced into a reaction vessel provided with a stirrer, thermometer and gas inlet tube.

After expelling the air from the reaction vessel by oxygen, the stirrer was switched on and pure oxygen was passed into the mixture at 70° C. under normal pressure, while stirring vigorously. After 15 minutes, 0.05 mole of O$_2$ had been taken up and the uptake of oxygen ceased.

After filtering off the catalyst, the content of phenylglyoxylic acid in the filtrate was determined by differential pulse polarography. 1 N LiOH was used as the base electrolyte. The determination was carried out against phenylglyoxylic acid solution of known content, which was added as an internal standard during a repeat measurement. The determination gave a phenylglyoxylic acid yield of 99.3% of theory.

The phenylglyoxylic acid could also be liberated by acidifying the mixture with sulphuric acid, extracted from the solution, for example with ether, and, after evaporating off with ether, obtained in the free form. The catalyst, which had been filtered off, could be re-used.

The procedure followed was as in Example 1, except for the difference that the concentration of mandelic acid and sodium hydroxide solution was increased. The volume of sodium hydroxide solution (100 ml), the amount of platinum-containing active charcoal (0.75 g containing 1% by weight of Pt), the amount of lead ($5 \times 10^{-5}$ mole in the form of lead nitrate), the temperature (70° C.) and the pressure (1 bar) remained the same.

The concentrations of mandelic acid and NaOH, the amounts of NaOH, platinum and lead employed per mole of mandelic acid, the phenylglyoxylic acid yields achieved and the reaction times applied to obtain them are indicated in Table 1.

Table 1:

| Example No. | Mandelic acid mols | Normality of the NaOH (100 ml) | Amount employed per mol of mandelic acid | | | Reaction time (hours) | Yield % of theory |
| | | | NaOH (mols) | Platinum (mg) | Lead (mols) | | |
| --- | --- | --- | --- | --- | --- | --- | --- |
| 1[(a)] | 0.1 | 1.2 | 1.20 | 75 | $5 \times 10^{-4}$ | 0.25 | 99.3 |

Table 1:-continued

| Example No. | Mandelic acid mols | Normality of the NaOH (100 ml) | Amount employed per mol of mandelic acid | | | Reaction time (hours) | Yield % of theory |
| --- | --- | --- | --- | --- | --- | --- | --- |
| | | | NaOH (mols) | Platinum (mg) | Lead (mols) | | |
| 2 | 0.15 | 1.7 | 1.13 | 50 | $3.3 \times 10^{-4}$ | 0.43 | 99.1 |
| 3 | 0.20 | 2.2 | 1.10 | 37.5 | $2.5 \times 10^{-4}$ | 0.78 | 99.0 |
| 4 | 0.25 | 2.7 | 1.08 | 30 | $2 \times 10^{-4}$ | 1.13 | 98.5 |
| 5 | 0.03 | 3.2 | 1.07 | 25 | $1.7 \times 10^{-4}$ | 2.25 | 98.0 |

(a)Included in the table for comparison

EXAMPLES 6 TO 10

The procedure followed was as in Example 1, except for the difference that 38 g (0.25 mol) of mandelic acid, 100 ml of 2.7 N NaOH and various amounts of activator (lead(II) nitrate) were employed.

The amount of platinum-containing active charcoal (0.75 g with a Pt content of 1% by weight), the temperature (70° C.) and the pressure (1 bar) remained the same.

The amounts of lead (in moles) employed per mole of mandelic acid, the phenylglyoxylic acid yields and the reaction times applied to obtain them are indicated in Table 2.

Table 2

| Example No. | Amount of lead employed per mol of mandelic acid (mols) | Reaction time (hours) | Phenylglyoxylic acid yield (% of theory) |
| --- | --- | --- | --- |
| 6 | $2 \times 10^{-3}$ | 1.4 | 98.1 |
| 7 | $1 \times 10^{-3}$ | 1.1 | 98.9 |
| 8 | $1 \times 10^{-4}$ | 1.5 | 98 |
| 9 | $2 \times 10^{-5}$ | 2.5(a) | 86(a) |
| 10(c) | 0 | 2.5(b) | 0 |

(a)Oxidation prematurely interrupted after this time
(b)Virtually no uptake of O2
(c)Example 10 is a Comparison Example, which shows that virtually no oxidation occurs without the addition of an activator.

EXAMPLES 11 TO 13

The procedure followed was as in Example 1, except for the difference that 38 g (0.25 mole) of mandelic acid, 100 ml of 2.7 N NaOH, $2.5 \times 10^{-4}$ moles of Pb(NO$_3$)$_2$ in the form of a 0.5 molar solution and various reaction temperatures were used.

The amount of platinum-containing active charcoal (0.75 g containing 1% by weight of platinum) and the O$_2$ pressure (1 bar) remained the same.

The yields achieved, as a function of the temperature, and the reaction times applied to obtain them are indicated in Table 3:

Table 3

| Example No. | Temperature (°C.) | Reaction time (hours) | Phenylglyoxylic acid yield (% of theory) |
| --- | --- | --- | --- |
| 11 | 40 | 1.4 | 99.5 |
| 12 | 60 | 1.2 | 98.9 |
| 13 | 80 | 1.8 | 96.5 |

EXAMPLES 14 TO 20

The procedure corresponded to that of Example 1. 0.75 g of a platinum-containing active charcoal (so-called decolorizing charcoal with a platinum content of 1% by weight), a solution of 15.2 g (0.1 mole) of D,L-mandelic acid in 100 ml of sodium hydroxide solution of varying normality and lead(II) nitrate in the form of a 0.05 molar solution were initially successively introduced. The oxidation was carried out at 30° C. and under an O$_2$ pressure of 1 bar until 0.05 mol of O$_2$ had been taken up.

The yields achieved, as a function of the molar ratio of NaOH/mandelic acid, at various molar ratios of lead/mandelic acid and the reaction times applied to obtain them are indicated in Table 4:

Table 4

| Example No. | Molar ratio of NaOH/ mandelic acid | Molar ratio of lead$^{2+}$/ mandelic acid | Reaction time (hours) | Phenylglyoxylic acid yield (% of theory) |
| --- | --- | --- | --- | --- |
| 14 | 1.5 | $2.5 \times 10^{-5}$ | 2 | 99 |
| 15 | 1.5 | $2.5 \times 10^{-4}$ | 0.5 | 99 |
| 16 | 1.75 | $2.5 \times 10^{-4}$ | 0.5 | 98 |
| 17 | 2.0 | $2.5 \times 10^{-4}$ | 0.5 | 94 |
| 18 | 2.5 | $2.5 \times 10^{-3}$ | 0.5 | 95 |
| 19 | 3.0 | $2.5 \times 10^{-3}$ | 0.5 | 86 |
| 20 | 4.0 | $2.5 \times 10^{-3}$ | 0.5 | 84 |

EXAMPLE 21

The procedure corresponded to that of Example 1. 0.75 g of active charcoal with a platinum content of 1% by weight, a solution of 38 g (0.25 mol) of D,L-mandelic acid in 100 ml of 3 N sodium hydroxide solution and $1 \times 10^{-4}$ mole of Pb(NO$_3$)$_2$ were initially introduced into the oxidation apparatus. The oxidation was carried out at 70° C. and under an O$_2$ pressure of 1 bar until the stoichiometrically required amount of oxygen (0.125 mol) had been taken up.

After separating off the catalyst, this was employed again for the oxidation of mandelic acid, that is to say it was again added to a mixture of 38 g (0.25 mol) of D,L-mandelic acid, 100 ml of 3 N NaOH and $1 \times 10^{-4}$ mole of Pb(NO$_3$)$_2$ and the oxidation was carried out as above. The catalyst which had been separated off was employed again for the oxidation, and so on. In total, the catalyst was used 10 times. The phenylglyoxylic acid yields in the experiments were always between 91 and 97%. As a result of re-using the catalyst, the amount of platinum employed per mole of mandelic acid had already fallen about 3 mg.

When this result was obtained, the experiments were discontinued.

EXAMPLE 22

The procedure followed was as described in Example 1, except for the difference that the $5 \times 10^{-5}$ moles of lead were not introduced into the reaction mixture in the form of a lead(II) nitrate solution, but were added in the form of finely powdered (a) metallic lead, (b) lead(II) oxide (c) lead(II) sulphate, (d) lead(II) acetate, (e) lead(II)/(IV) oxide (red lead) or (f) lead(IV) oxide. In all cases, the reaction time was again only 15 minutes and the yield was always over 99% of theory.

EXAMPLE 23

The procedure followed was as described in Example 1, except for the difference that instead of lead, $2 \times 10^{-4}$ mole of bismuth was added to the reaction mixture in the form of its finely powdered nitrate (Bi(NO$_3$)$_3$.5H$_2$O). After an oxidation time of 20 minutes, the stoichiometrically required amount of oxygen had been taken up. Polarographic determination gave a phenylglyoxylic acid yield of 98% of theory. After filtering off, the catalyst could be re-used. Without the addition of bismuth, no mandelic acid oxidation was observed in this time.

EXAMPLES 24 TO 25

The procedure followed was as in Example 1. A solution of 38 g (0.25 mol) of D,L-mandelic acid in 100 ml (0.27 mol) of 10% strength sodium hydroxide solution was oxidized in the presence of 0.75 g of active charcoal with a platinum content of 1% by weight at 70° C. with O$_2$ under a pressure of 1 bar. $2 \times 10^{-4}$ mole of Bi(NO$_3$)$_3$.5 H$_2$O was also added to the reaction mixture before the oxidation. The oxidation took 1.25 hours. Thereafter, 0.125 mol of oxygen had been taken up and the phenylglyoxylic acid yield was 96% of theory. If the reaction was carried out at 40° C., the reaction time was 4.4 hours and the yield was 97% of theory.

EXAMPLE 26

The procedure followed was as in Example 1. A solution of 15.2 g (0.1 mol) of D,L-mandelic acid in 100 ml of 1.7 N sodium hydroxide solution was oxidized. 0.75 g of active charcoal (medicinal charcoal) with a palladium content of 7.5% by weight and $2.5 \times 10^{-5}$ mol of Pb(NO$_3$)$_2$ were added to the solution. Oxidation was then carried out at 65° C. and under an oxygen pressure of 1 bar. After 3.5 hours, 0.05 mol of O$_2$ had been taken up and the yield of phenylglyoxylic acid was 46% of theory.

Without the addition of lead and under conditions which were otherwise the same, virtually no uptake of oxygen (oxidation) could be detected in this time.

EXAMPLE 27

The procedure followed was as in Example 1. A solution of 15.2 g (0.1 mol) of D,L-mandelic acid in 100 ml of 2.0 N sodium hydroxide solution was oxidized. 1.5 g of active charcoal (medicinal charcoal) with a palladium content of 5% and $2 \times 10^{-4}$ mole of Bi(NO$_3$)$_3$.5 H$_2$O were added to the solution. Oxidation was then carried out at 70° C. and under an O$_2$ pressure of 1 bar. After 10 minutes, 0.05 mol of O$_2$ had been taken up and the phenylglyoxylic acid yield was 50% of theory.

Without the addition of lead and under conditions which were otherwise the same, no uptake of O$_2$ (oxidation) was observed.

EXAMPLE 28

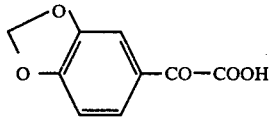

The procedure followed was as in Example 1. 0.75 g of active charcoal with a platinum content of 1% by weight and 0.1 g of Bi(NO$_3$)$_3$.5 H$_2$O ($2 \times 10^{-4}$ mole) were added to a solution of 39.2 g (0.2 mole) of 3,4-methylenedioxy-D,L-mandelic acid in 100 ml of 2.2 N sodium hydroxide solution. Oxidation was then carried out at 70° C. and under an O$_2$ pressure of 1 bar. After 2 hours, 0.1 mol of oxygen had been taken up and the oxidation ceased.

After filtering off the catalyst, the filtrate was acidified to pH 1 with 20% strength hydrochloric acid and cooled to about 10° C. and the product which had precipitated was filtered off, washed with ice-water and dried. 38.2 g of 98.5% pure 3,4-methylenedioxy-phenylglyoxylic acid, melting point 144°–146° C., were obtained. Yield: 97% of theory.

EXAMPLE 29

0.5 ml of 0.5 molar Pb(NO$_3$)$_2$ solution ($2.5 \times 10^{-3}$ mole of Pb) and a solution of 19.6 g (0.1 mol) of 3,4-methylenedioxy-mandelic acid in 100 ml of 1.5 N sodium hydroxide solution were added to 0.75 g of active charcoal with a platinum content of 1% by weight. Oxidation was then carried out at 70° C. and under an O$_2$ pressure of 1 bar, as described in Example 1. After 25 minutes, 0.05 mol of oxygen had been taken up and the oxidation ceased. The catalyst was filtered off and the filtrate was acidified to pH 1 with 20% strength hydrochloric acid and cooled with ice. The 3,4-methylenedioxy-phenylglyoxylic acid which had precipitated was filtered off, washed with ice-water and dried: 18.2 g (purity: about 99%), melting point: 144°–146° C.

About a further 1.5 g of the same acid (purity about 80%), melting point: 127°–138°, could be isolated from the mother liquor by extraction with ether.

Total yield: 99% of theory.

EXAMPLE 30

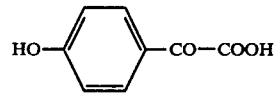

A solution of 8.4 g (0.05 mol) of 4-hydroxy-D,L-mandelic acid in 100 ml of 2 N sodium hydroxide solution was added to 1 g of active charcoal with a platinum content of 1% and, after adding $2.5 \times 10^{-3}$ mol of Pb(NO$_3$)$_2$, was oxidized at 30° C. and under an oxygen pressure of 1 bar. After 40 minutes, about 0.021 mol of oxygen had been taken up. Polarographic determination carried out after filtering off the catalyst gave a yield of 83% of theory of 4-hydroxy-phenylglyoxylic acid.

EXAMPLE 31

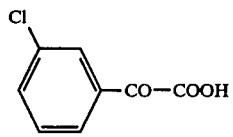

A solution of 18.6 g (0.1 mol) of 3-chloro-D,L-mandelic acid in 100 ml of 1.5 N sodium hydroxide solution was added to 0.95 g of active charcoal with a platinum content of 1% and, after adding $2.5 \times 10^{-3}$ mol of Pb(NO$_3$)$_2$, was oxidized at 70° C. and under an O$_2$ pressure of 1 bar. After 25 minutes, when 0.05 mol of O$_2$ had been taken up, the catalyst was filtered off. Polarographic determination gave a 3-chloro-phenylglyoxylic acid yield of 87.9% of theory.

16.2 g of 3-chloro-phenylglyoxylic acid, melting point 59°-62° C., could be isolated from the solution by acidifying with 20% strength hydrochloric acid, cooling with ice-water, filtering off and drying.

EXAMPLE 32

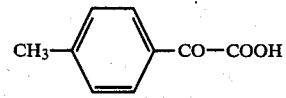

The procedure followed was as in Example 1, except with the difference that 8.3 g (0.05 mol) of 4-methyl-D,L-mandelic acid, dissolved in 50 ml of 1.5 N sodium hydroxide solution and in the presence of 0.4 g of active charcoal with a platinum content of 1% by weight and 0.25 ml of 0.5 molar lead(II) nitrate solution ($\triangleq 1.25 \times 10^{-4}$ mol of Pb), were oxidized at 70° C. under an $O_2$ pressure of 1 bar, while mixing thoroughly. After 40 minutes, 0.025 mol of oxygen had been taken up and the oxidation ceased. After filtering off the catalyst, polarographic determination of the filtrate against pure p-tolylglyoxylic acid gave a yield of 93% of theory.

On acidifying the filtrate to pH 1, p-tolylglyoxylic acid first precipitated as an oil, which could be extracted by shaking with ether. After evaporating off the ether, about 7.5 g of p-tolylglyoxylic acid of melting point 84°-86° C. remained, from which pure p-tolylglyoxylic acid of melting point 98°-99° C. could be obtained by sublimation in vacuo.

EXAMPLE 33

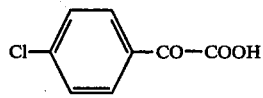

The procedure followed was as in Example 1, except for the difference that 18.6 g (0.1 mol) of 4-chloro-D,L-mandelic acid, dissolved in 100 ml of 1.35 N sodium hydroxide solution and after adding 1 g of active charcoal with a platinum content of 1% by weight and 0.5 ml of 0.5 molar $Pb(NO_3)_2$ solution ($\triangleq 2.5 \times 10^{-4}$ mole of lead), were oxidized at 70° C. and under an $O_2$ pressure of 1 bar, while mixing thoroughly. After 60 minutes, 0.05 mole of $O_2$ had been taken up, and after filtering off the catalyst, polarographic determination of the filtrate against pure 4-chloro-phenylglyoxylic acid as an internal standard gave a yield of 4-chloro-phenylglyoxylic acid of 86.5% of theory.

The 4-chloro-phenylglyoxylic acid could be precipitated by acidifying with HCl and recrystallized from water: melting point 61°-62° C. On recrystallization from ligroin and after thorough drying, the anhydrous form with a melting point of 91°-92° C. was obtained.

It will be understood that the specification and examples are illustrative but not limitative of the present invention and that other embodiments within the spirit and scope of the inventiion will suggest themselves to those skilled in the art.

What is claimed is:

1. Process for the preparation of an arylglyoxylic acid compound which comprises oxidizing an α-hydroxyarylacetic acid of the formula

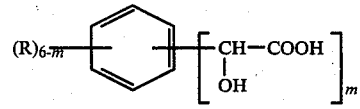

in which m is 1, 2 or 3, each R individually is hydrogen, alkyl, cycloalkyl, aryl, aralkyl, alkoxy, cycloalkoxy, aryloxy, hydroxyl, halogen, aminoalkyl or carboxyl, with the proviso that two R's together can represent the methylenedioxy group which process comprises oxidizing said α-hydroxyarylacetic acid with oxygen or a gas containing molecular oxygen in aqueous alkaline medium in the presence of a catalyst comprising a platinum-group metal in the presence as an activator of at least one of lead, a lead compound, bismuth and a bismuth compound at a temperature of up to the boiling point of the resulting reaction mixture.

2. Process as claimed in claim 1 wherein said oxidizing is carried out in the presence of an inert organic solvent.

3. Process as claimed in claim 1 wherein m is 1.

4. Process as claimed in claim 1 wherein m is 2.

5. Process as claimed in claim 1 wherein m is 3.

6. Process as claimed in claim 1 wherein each R is hydrogen.

7. Process as claimed in claim 1 wherein at least one R is hydrocarbyl or hydrocarbyloxy of up to 6 carbon atoms each.

8. Process as claimed in claim 1 wherein at least one R is halogen.

9. Process as claimed in claim 1 wherein at least one R is aminoalkyl.

10. Process as claimed in claim 1 wherein at least one R is carboxyl.

11. Process as claimed in claim 1 wherein two R's together represent a methylenedioxy group.

12. Process as claimed in claim 1 wherein the lead and/or bismuth content amounts to $5 \times 10^{-6}$ to $1 \times 10^{-1}$ mole per mole of α-hydroxyacetic acid group to be oxidized.

13. Process as claimed in claim 1 wherein the lead and/or bismuth content amounts to $1 \times 10^{-5}$ to $1 \times 10^{-2}$ mole per mole of α-hydroxyacetic acid group to be oxidized.

14. Process as claimed in claim 1 wherein the lead and bismuth are in elemental form.

15. Process as claimed in claim 1 wherein the lead and/or bismuth are in the form of an oxide or a salt of a hydracid, an inorganic oxyacid, a transition-metal-containing oxyacid or an organic aliphatic or aromatic acid.

16. Process as claimed in claim 1 wherein said platinum-group metal catalyst is at least one of platinum and palladium.

17. Process as claimed in claim 1 wherein the said lead and/or bismuth are incorporated into the platinum-group metal catalyst.

18. Process as claimed in claim 1 wherein the platinum-group metal catalyst is a supported catalyst.

19. Process as claimed in claim 1 wherein active charcoal is used as the support for the platinum-group metal.

20. Process as claimed in claim 1 wherein the platinum-group metal content of the supported catalyst is less than 10% by weight.

21. Process as claimed in claim 1 wherein the platinum-group metal content of the supported catalyst is 0.1 to 2.5% by weight.

22. Process as claimed in claim 1 wherein less than 500 mg of platinum-group metal is employed per mole of a α-hydroxyacetic acid group.

23. Process as claimed in claim 22 wherein 10–150 mg of platinum-group metal are employed per mole of α-hydroxyacetic acid group.

24. Process as claimed in claim 1 wherein sodium hydroxide or potassium hydroxide is employed as the alkali.

25. Process as claimed in claim 1 wherein the alkali is employed in an amount of 0.3 to 5 equivalents per mole of carboxyl group in the α-hydroxyacetic acid (I) to be oxidized.

26. Process as claimed in claim 25 wherein the alkali is employed in an amount of 0.5 to 2.5 equivalents per mole of carboxyl group in the α-hydroxyacetic acid (I) to be oxidized.

27. Process as claimed in claim 1 wherein the alkali is employed in an amount of 0.9 to 1.8 equivalents per mole of carboxyl group in the α-hydroxyacetic acid (I) to be oxidized.

28. Process as claimed in claim 1 wherein it is carried out at temperatures of from 0° to 100° C.

29. Process as claimed in claim 1 wherein it is carried out with oxygen or an oxygen-containing gas under a pressure of 0.5–10 bars.

30. Process as claimed in claim 1 wherein a compound of the formula (I) is employed wherein m represents the number 1 and the R's, independently of one another, each represent hydrogen, alkyl with 1 to 12 C atoms, cycloalkyl with 3 to 6 C atoms, phenoxy, hydroxyl, fluorine, chlorine, bromine, iodine, aminoalkyl with 1 to 4 C atoms or the carboxyl group, it also being possible for two R's together to represent the methylenedioxy group.

31. Process as claimed in claim 1 wherein phenylglyoxylic acid is prepared by oxidizing mandelic acid.

* * * * *